United States Patent [19]

Nagasawa et al.

[11] Patent Number: 4,627,274
[45] Date of Patent: Dec. 9, 1986

[54] APPARATUS FOR TESTING STABILITY OF HEAVY OIL

[75] Inventors: Takao Nagasawa, Kawasaki; Satoru Uchida, Matsudo, both of Japan

[73] Assignee: Nippon Oil Company, Limited, Japan

[21] Appl. No.: 749,471

[22] Filed: Jun. 21, 1985

[30] Foreign Application Priority Data

Jun. 27, 1984 [JP] Japan .................... 59-95266
Jun. 3, 1985 [JP] Japan .................... 60-82518

[51] Int. Cl.$^4$ ........................................ G01N 33/28
[52] U.S. Cl. ........................................ 73/64; 73/54
[58] Field of Search ............. 73/64, 54; 436/162; 422/70, 68

[56] References Cited

U.S. PATENT DOCUMENTS

| | | | |
|---|---|---|---|
| 2,302,224 | 11/1942 | Jones | 73/54 |
| 2,946,216 | 7/1960 | Elliott et al. | 73/64 |
| 3,049,964 | 8/1962 | Miller et al. | 73/64 |
| 3,093,997 | 6/1963 | Uhrmacher | 73/54 |
| 3,843,053 | 10/1974 | Thoden | 436/162 |
| 4,351,800 | 9/1982 | Kopp et al. | 422/70 |

OTHER PUBLICATIONS

Standard Test Method for "Compatibility of Fuel Oil Blends by Spot Test", Designation: D 2781-82, pp. 675-677.

Nisseki Technical Review 1983, vol. 25/No. 5, pp. 22-28.

Primary Examiner—Michael J. Tokar
Assistant Examiner—Hezron E. Williams
Attorney, Agent, or Firm—Lowe, Price, LeBlanc, Becker & Shur

[57] ABSTRACT

Electric heating means is arranged in the bottom portion of one case body, and an air bath tank and a sample heating tank, communicating with each other, are formed within this case body. The temperature of air in the air bath tank is maintained at a predetermined level by a temperature detecting element and a temperature controlling device. A filter paper is held in the air bath tank by supporting means at a position above the heating means spaced by a predetermined distance from the heating means. A heavy oil sample heated at a predetermined temperature for a predetermined time in the sample heating tank is dropped on the filter paper and the filter paper is dried for a predetermined time. The stability of the heavy oil is evaluated based on the state of spreading of the dropped heavy oil on the filter paper.

20 Claims, 9 Drawing Figures

4,627,274

APPARATUS FOR TESTING STABILITY OF HEAVY OIL

BACKGROUND OF THE INVENTION (1) Field of the Invention

The present invention relates to an apparatus for testing the stability of heavy oil. More particularly, the present invention relates to an apparatus suitable for testing the stability of heavy oil not only in a well-equipped laboratory but also in other places, for example, on a vessel.

(2) Description of the Prior Art

In the field of marine business and the like, the problem of the quality of fuels has attracted worldwide attentions, and various efforts have been made to cope with troubles owing to fuel oils and improve the quality of fuels.

What is most important among properties of marine heavy oil is the stability having a close relation to formation of sludge in heavy oil, and also the method of evaluation of this stability is important.

We made researches with a view to developing a simple method of testing the stability of heavy oil having a good conformity with occurrence of a trouble in a centrifugal cleaner, strainer or storing tank in the field and being adoptable for ordinary quality control. As the result, we found that a novel spot test method based on the ASTM spot test (ASTM D-2781-82) and improved to expand the application range has a good conformity with the actual working state and the stability can be simply evaluated according to this method.

This novel spot test method is introduced on pages 22 and 23 of Nisseki Technical Review, Volume 25, No. 5 (published in December 1983 by Nippon Oil Co., Ltd.).

The operation procedures of this spot test method are summarized below.

(1) A heavy oil sample is maintained at a temperature of 90° to 100° C. for 15 to 20 minutes and stirred sufficiently.

(2) One drop of the sample is caused to fall on the central part of a horizontally held filter paper (a filter paper for chromatography) by using a glass rod (having a diameter of 4 to 6 mm and a length of 150 to 200 mm and having the top end rounded by annealing).

(3) The sample-dropped filter paper is kept in the horizontal state and placed in a air bath tank maintained at a temperature of 100°±2° C., and is dried for 1 hour.

(4) The filter paper is taken out from the air bath tank, and the spot of the sample spread on the filter paper is compared with reference spots with respect to the form and characteristics and stability of a reference spot conformable to the sample spot is selected.

No particular problem arises when the stability of heavy oil is evaluated in a chemical laboratory according to this method, but if this test method is carried out on a vessel having no experimental equipment, various experimental tools and devices become necessary and the test cannot be performed simply.

SUMMARY OF THE INVENTION

It is a primary object of the present invention to provide a compact apparatus for testing stability of heavy oil in which all the facilities necessary for carrying out the above-mentioned novel spot test method are collectively and simply arranged and the above-mentioned disadvantage of the novel spot test method is eliminated.

According to the present invention, an air bath tank which a temperature of the air therein is controlled at a predetermined level and a sample heating tank are arranged in one case body so as to communicate with each other, and at least one electric heating means is disposed in the bottom portion of this case body. A heavy oil sample placed in a sample vessel is heated at a predetermined temperature, for example, 90° to 100° C., in the sample heating tank, and this state is maintained for 15 to 20 minutes and the sample is sufficiently stirred. In the air bath tank, the temperature in the tank is detected by a temperature detecting element disposed in the tank, the quantity of the electric current supplied to the above-mentioned heating means is controlled by temperature controlling means so that the temperature of the air in the tank is maintained at a predetermined level, for example, 100°±2° C. One drop of the heated heavy oil sample in the sample vessel is caused to fall on a filter paper supported in the air bath tank by supporting means, and the sample-dropped filter paper is dried for about one hour. The spot spread on the filter paper is observed and the stability of the the heavy oil sample is evaluated. It is preferred that this evaluation be made by comparison with a reference spot.

According to the present invention, a thermostat switch can be used as means for detecting the air temperature in the air bath tank. This thermostat switch is connected in series to a circuit for supplying an electric current to the heating means to control the air temperature in the air bath tank to a predetermined level.

Furthermore, according to the present invention, the air bath tank and the sample heating tank may be substantially closed to improve the heating efficiency of the heating means.

According to the present invention, by arranging one compact testing apparatus in an appropriate place, the novel heavy oil stability spot test proposed by us can be carried out very easily, and the apparatus of the present invention is suitable for the field test in a vessel or the like where the experimental equipment is not sufficient.

The structure and features of the present invention will now be described in detail with reference to embodiments thereof.

DETAILED DESCRIPTION OF THE PREFERRED EMBODIMENTS

Figure 1:
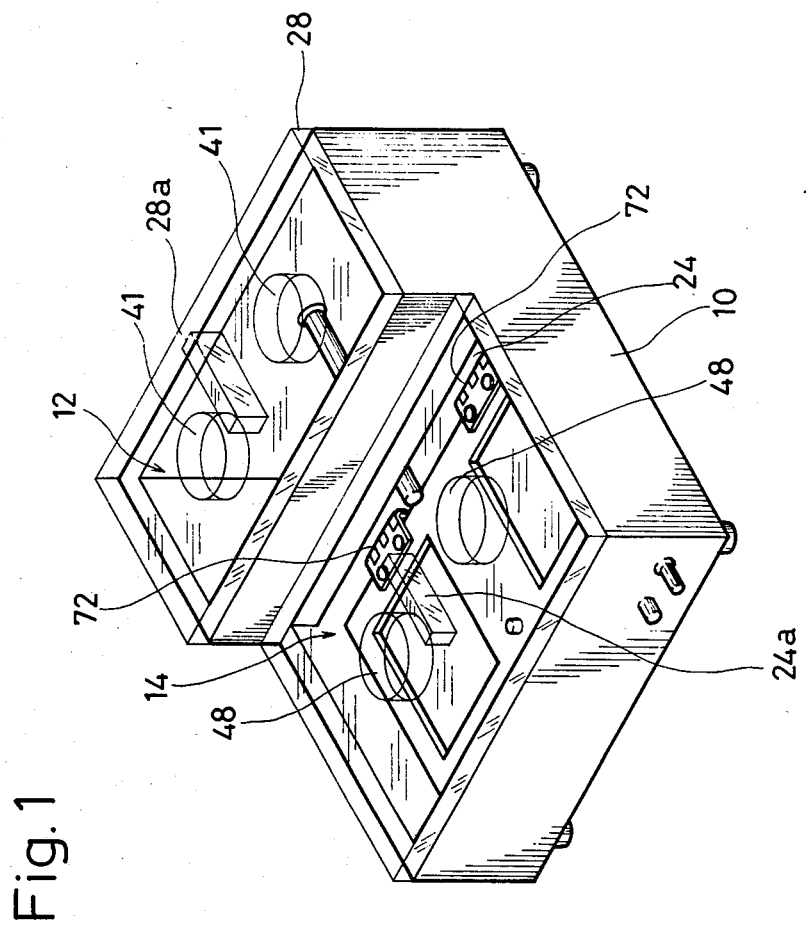
FIG. 1 is a perspective view illustrating a heavy oil stability testing apparatus according to the first embodiment of the present invention.
Figure 2:
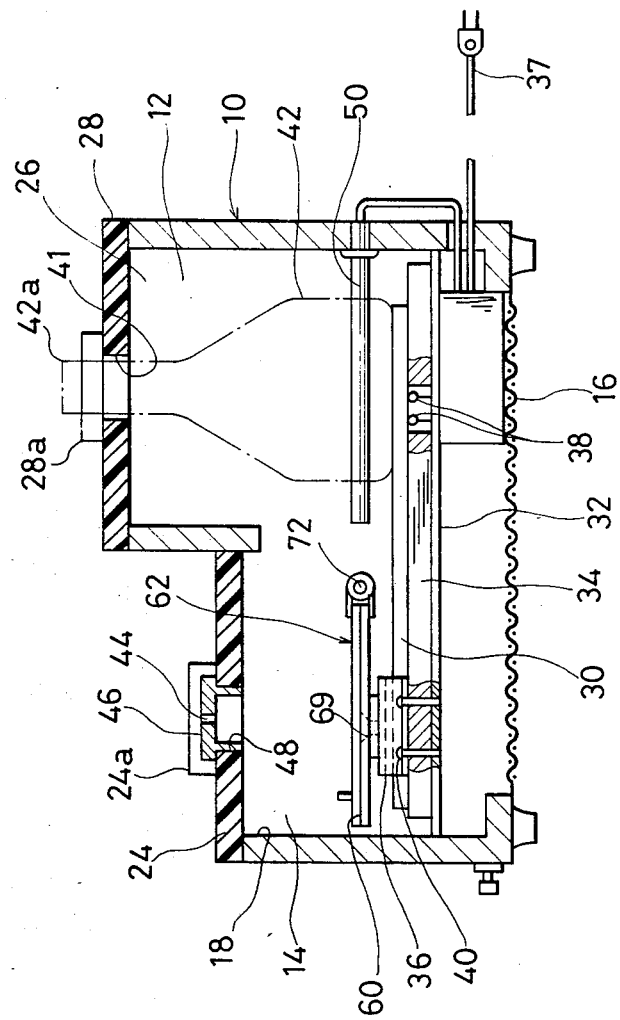
FIG. 2 is a view showing the longitudinal section of the testing apparatus shown in FIG. 1 along the longitudinal direction.

Referring to FIGS. 1 and 2, a case body 10 comprises a sample heating tank 12 and an air bath tank 14, which are arranged in parallel in the lateral direction in the case body 10. The bottom face of the case body 10 is opened and a metal net member 16 is secured to the inner circumferential face of the case body 10 to cover the open face. The top face of a top opening 18 of the air bath tank 14 is covered with a cover 24 on the peripheral top end of the tank 14. The cover 24 is formed of a heat-resistant transparent plastic material. The top opening 18 is substantially closed by the cover 24. The top face of a top opening 26 of the sample heating tank 12 is covered with a cover 28 on the peripheral top end of the tank 14. The cover 28 is formed of a heat-resistant transparent plastic material and the top opening 26 is substantially closed by the cover 28.

A holding plate 32 extending in the horizontal direction in the shelf-like form is attached and secured to the inner wall of the bottom portion of the case body 19 at a position of a predetermined height. A heating plate 30 is placed on the top face of the hold plate 32 through an asbestos plate 34 as a heat insulating member and is horizontally held.

The heating plate 30 comprises a plate of a metal such as iron or aluminum and an electric heater (not shown) embedded in the metal plate. Incidentally, the heating plate 30 and asbestos plate 34 are secured to the holding plate 32 by a supporting leg 36 described below.

A power source terminal 38 of the electric heater is exposed to the space of the bottom portion of the case body 10 through the asbestos plate 34 and is connected to a power source cord 37 which is connected to the power source through the side wall of the case body 10 from said space and to a thermostat switch 50 for performing on-off control of the power source circuit 80 (FIG. 6) for the heating plate 30, as described hereinafter.

The air bath tank 14 is constructed to have a flat space of a low height, and the sample heating tank 12 is formed in a space, the height of which is higher than that of the air bath tank 14. Both the tanks 12 and 14 are arranged to communicate with each other in their bottom portion.

Figure 3:
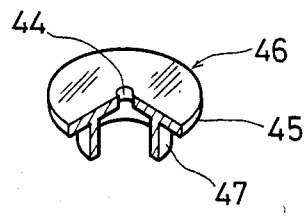
FIG. 3 is a perspective view showing a lid member constituting a part of a cover of an air bath tank in the testing apparatus shown in FIG. 1.

Two openings 41 are formed through the top face cover 28 of the sample heating tank 12 so that open top ends 42a of two sample vessels, for example, Erlenmeyer flasks 42, can pierce through the openings 41, respectively. Two sample dropping openings 48 are formed on the top face cover 24 of the air bath tank 14 so that the openings 48 can be opened or closed by a lid member 46 having a small hole 44 communicating with the outer and inner sides of the tank 14 (see FIGS. 2 and 3). As shown in FIG. 3, the lid member 46 comprises a disc portion 45 having the small hole 44 formed at the center and a cylindrical portion 47 contiguous to the lower face of the disc portion 45. The cylindrical portion 47 is fitted in the sample dropping opening 48. The small hole 44 is formed so as to liberate hot air present in the upper portion of the tank 14 and uniformalize the temperature within the tank 14.

Knobs 24a and 28a are attached to the top faces of the two covers 24 and 28, respectively.

In the air bath tank 14, a filter paper holding member 62 is secured and held onto the inner wall of the case body 10 to hold a filter paper 60 horizontally at a position about 5 mm above the heating surface of the heating plate 30.

Figure 4:
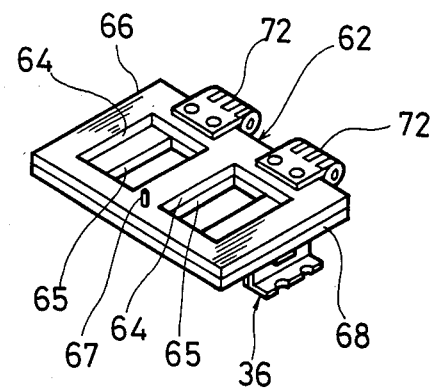
FIG. 4 is a perspective view showing an example of filter paper supporting means in the testing apparatus shown in FIG. 1.

As shown in FIG. 4, the filter paper holding member 62 has a structure in which the filter paper 60 is inserted and gripped between an upper plate 66 and a lower plate 68, each having two each of rectangular openings 64 and 65 for exposing the sample-dropped portion of the filter paper to the position corresponding to the sample dropping opening 48. One side of the upper plate 66 is connected to one side of the lower plate 68 through hinges 72 arranged at two points so that they can be optionally opened and closed.

The opening 64 of the upper plate 66 is formed to have a square shape and the opening 65 of the lower plate 68 is formed to have an oblong shape having the longer side equal to a side of the opening 64. Accordingly, the filter paper 60 held between the upper plate 66 and lower plate 68 is exposed in the square shape, and the portion of the filter paper placed on top face of a part of the lower plate 68 projecting to the opening 64 of the side of the upper plate 66 is used as an area for recording data of the spot test described hereinafter, and the above-mentioned partial face acts as an underlying cardboard for recording the test data on the filter paper. A knob 67 is attached to the upper plate 66 and the above-mentioned opening and closing are performed by picking up the knob 67 between a pair of tweezers or the like.

Figure 5:
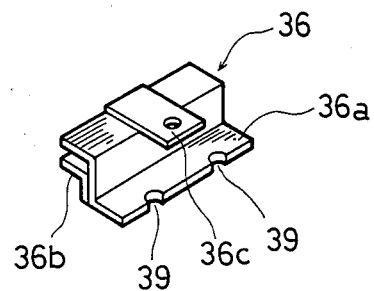
FIG. 5 is a perspective view showing heating plate supporting means in the testing apparatus shown in FIG. 1.

The supporting leg 36 is attached and secured to each of both the ends of the lower plate 68 with respect to the longitudinal direction. As shown in FIG. 5, the supporting leg 36 comprises a substantially Z-shaped plate member 36 bent at a right angle at two positions, a plate member 36b secured to the inner face of the vertical part of the plate member 36a in a manner extending in parallel to the horizontal part of the plate member 36a and a plate member 36c secured to the center of the top end face of the plate member 36a in a manner extending outward in parallel to the horizontal part of the plate member 36a. The supporting leg 36 is attached and secured to the asbestos plate 34 and holding plate 32 by screwing a screw 40 engaged with a groove 39 formed on the outer end edge of the lower horizontal part of the substantially Z-shaped plate member 36a into the portion of the asbestos plate 34 extending around the heating plate 30 and the holding plate 32, whereby the asbestos plate 34 and holding plate 32 are secured and fixed.

Both the end portions of the lower plate 68 with respect to the longitudinal direction are attached and secured to the plate member 36c of the supporting leg 36, whereby the filter paper holding member 62 is fixed and held in the air bath tank 14.

A thermostat switch 50 for performing on-off control of a circuit 80 for supplying an electric current to the heating plate 30 (see FIG. 6) to maintain the surface of the filter paper at a predetermined level, for instance about 100° C., is connected in series to the electric heater in the heating plate 30. Thus, the means for controlling the air temperature in the air bath tank 14 is constructed.

The thermostat switch 50 has a rod-like shape and acts as a temperature detecting element, and the thermostat switch 50 is attached through the side wall of the sample heating tank 12 of the case body 10 and extends to the central portion of the heating plate 30 through between the two Erlenmeyer flasks 42 in such a manner that a predetermined clearance is formed between the heating face of the heating plate 30 and the thermostat switch 50. Incidentally, the thermostat switch 50 is disposed at a point in which the air temperature in the air bath tank 14 is most clearly reflected, and the thermostat switch 50 may be constructed by a bimetal switch or a switch utilizing expansion and contraction of a wax.

The operation of the spot test using the testing apparatus having the above-mentioned structure will now be summarized.

(1) The Erlenmeyer flask 42 charged with a sample was set in the sample heating tank 12 and the cover 28 is attached to the tank 12, and the sample was maintained at 90° to 100° C. for 15 to 20 minutes and was sufficiently stirred.

(2) The lid member 46 of the cover 24 of the air bath tank 14 is taken out, and one drop of the sample in the Erlenmeyer flask 42 was caused to fall on the filter paper 60 held on the filter paper holding member 62 from each sample dropping opening 48 by a glass rod. Then, the lid member 46 is placed on each sample dropping opening 48.

(3) The sample-dropped filter paper 60 is maintained at 100°±2° C. and dried for 1 hour.

(4) The filter paper 60 is taken out from the filter paper holding member 62, and the spot-like spreading state of the sample on the filter paper is examined. In this case, judgement may be empirically made, but precise judgement can be performed by comparing the spot with a reference spot prepared in advance. In the spot on the filter paper, the density and thickness of the background ring and the inner ring appearing at the center of the background ring are changed by the influence of sludge of the heavy oil, and the stability of the heavy oil can be clearly judged by this spot. The testing method according to the present invention is characterized in that the influence of a wax component in heavy oil can be eliminated by heating and the test can be performed even on a sample having a high viscosity.

The above-mentioned apparatus for testing the stability of heavy oil has a compact structure in which all the equipment facilities necessary for the spot test are collectively arranged, and therefore, the testing apparatus can be simply and conveniently used even on a vessel without arranging various test tools for the test, and the spot test can be performed very smoothly in any place at any time and the operation efficiency of the spot test can be highly improved.

It is preferred that a standard spot diagram be appended to the above-mentioned apparatus for testing the stability of heavy oil.

Moreover, according to the above-mentioned apparatus for testing the stability of heavy oil, since the thermostat switch 50 for performing on-off control of the circuit 80 for supplying an electric current to the heating plate 30 is adopted as the means for controlling the surface temperature of the air bath tank, a complicated structure in which a temperature detecting element and a temperature controlling device are independently disposed need not be adopted and the structure of the testing equipment can be greatly simplified.

Figure 7:
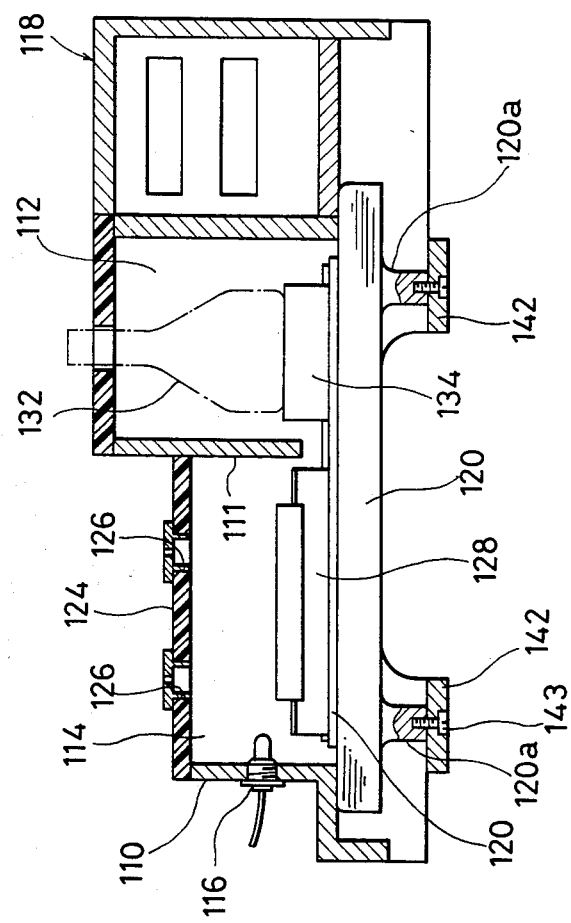
FIG. 7 is a view showing the longitudinal section of a testing apparatus according to the second embodiment of the present invention along the longitudinal direction.

FIG. 7 illustrates the second embodiment of the present invention. Portions different from those of the above-mentioned first embodiment will now be described.

Figure 6:
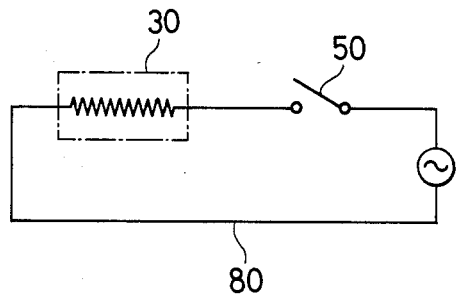
FIG. 6 is a circuit diagram illustrating a circuit for supplying an electric current to heating means in the testing apparatus shown in FIG. 1.

In this second embodiment, a partition plate 111 is arranged in a case body 110 so that a sample heating tank 112 and a air heating tank 114 are separated from each other in the upper space within the case body 110 and they communicate with each other in their lower portion. This partition plate 111 can be thus arranged so that the air temperature in the air heating tank 114 is hardly influenced by the sample heating tank 112, and control of the air temperature is facilitated. Accordingly, an element 116 for detecting the air temperature is arranged so that the detecting portion thereof is located within the lower space in the air tank 114 to precisely detect the temperature of air around the filter paper. The temperature detecting element 116 is a switch which is turned on and off with a predetermined temperature being as the boundary, such as a thermostat switch as used in the above-mentioned first embodiment, and a detection signal of the temperature detecting element 116 is put out into a temperature control device 118. The device 118 for supplying an electric current to an electric heater for the heating plate 120 may be constructed in the same electric circuit as shown in FIG. 6. In order to avoid super-heating of the temperature control device 118, the device is disposed and attached to the outer wall of the case body 110 at a portion apart from the heating plate 120.

Figure 8:
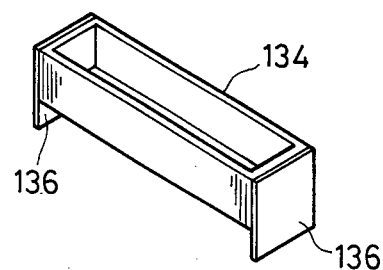
FIG. 8 is a perspective view showing a saucer member for receiving a sample vessel in the testing apparatus shown in FIG. 7.
Figure 9:
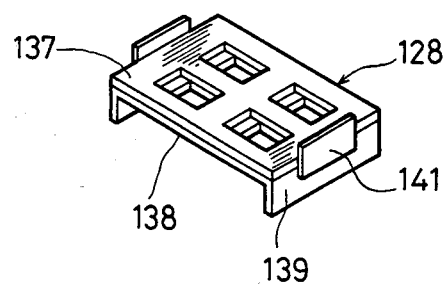
FIG. 9 is a perspective view illustrating filter paper supporting means in the testing apparatus shown in FIG. 7.

Four sample dropping openings 126 are formed on a cover 124 of the air bath tank 114, and a filter paper holding member 128 is dismountably arranged in the tank 114. An Erlenmeyer flask 132 is placed on the heating plate 120 through a saucer member 134 in the sample heating tank 112. As shown in FIG. 8, the saucer member 134 has a box-like shape having the open top end, and the saucer member 134 is set so that a supporting leg 136 extending downward from both the end walls of the saucer member 134 with respect to the longitudinal direction is fitted in a recess portion formed around the heating face of the heating plate 120. When the above-mentioned arrangement is adopted, for example, even if the Erlenmeyer flask having the bottom portion received in the saucer member 134 is broken by superheating by mistake, there is no risk of direct overflowing of the sample into the sample heating tank 112 and the test can be performed safely. As shown in FIG. 9, the filter paper holding member 128 has an upper plate 137 and a lower plate 138, each having four openings to expose a sample-dropping portion of the filter paper. A supporting leg 139 having a predetermined length is integrally formed on both the ends of the lower plate 138 to maintain the filter paper held between the upper plate 137 and lower plate 138 at a position elevated by a predetermined distance from the heating plate 120, and the supporting leg 139 is placed in a recess portion formed around the heating face to fix the filter paper holding member 128 at a predetermined position. A handle plate 141 extending upward is secured to each of both the ends of the lower plate 138. If the filter paper holding member 128 is dismountably attached to the case body 110 in the above-mentioned manner, attachment of the filter paper to the filter paper holding member 128 is facilitated and maintenance of the filter paper holding member 128 can be made easier.

A pair of legs 142 spacing from each other are formed on the open bottom face of the case body 110 like a bridge. The supporting legs 120a of the heating plate 120 are placed on this pair of the legs 142, and in this state, the legs 142 and the supporting legs 120a are secured by attachment means such as screws. In this case, the lower end of the side wall portion of the case body 110 on the side of the air bath tank 114 is placed on the peripheral face of the body portion of the heating plate 120, and the lower end of the outer wall of the sample heating tank 112 is similarly placed on the peripheral face of the heating plate 120, whereby the heating plate 120 is pressed from above and below and thus secured. In other words, the case body 110 is held on the heating plate 120.

Other structural features and functional effects are the same as described in the preceding embodiment.

We claim:

1. An apparatus for testing the stability of heavy oil, which comprises one case body within which a sample heating tank and an air bath tank, communicating with each other, are arranged in the lateral direction, at least one electric heating means arranged horizontally in the bottom portion of the case body, a temperature detecting element for detecting the temperature of air in said air bath tank, temperature control means for controlling the quantity of an electric current supplied to said heating means based on the detection value of said temperature detecting element so that the air temperature in said air bath tank is maintained at a predetermined level, a filter paper arranged in said air bath tank, on which a sample is dropped, filter paper holding means for maintaining said filter paper at a predetermined height in said air bath tank, a first cover covering the top face of said simple heating tank of said case body and having an opening in which the open top end portion of a sample vessel arranged in said heating tank is inserted, and a second cover covering the top face of said air bath tank of said case body and having a sample dropping opening, wherein a heavy oil sample heated in the sample vessel is dropped on the filter paper and the stability of heavy oil is determined based on the state of the spreaded heavy oil sample on the filter paper.

2. An apparatus for testing the stability of heavy oil according to claim 1, wherein said heating means is a plate member arranged horizontally to define bottom faces of said sample heating tank and said air bath tank.

3. An apparatus for testing the stability of heavy oil according to claim 2, wherein said filter member holding means comprises means for holding the filter paper at a position above said heating means by a predetermined distance therefrom.

4. An apparatus for testing the stability of heavy oil according to claim 1, wherein said heating means comprises a heating plate comprising a metal plate and an electric heater embedded therein.

5. An apparatus for testing the stability of heavy oil according to claim 4, wherein said heating means is thermally insulated from said case body by heat insulating means.

6. An apparatus for testing the stabiltiy of heavy oil according to claim 4, wherein said heating means is a heating plate secured and supported through a heat insulating plate on the top face of a holding plate supported horizontally on the bottom portion of said case body.

7. An apparatus for testing the stability of heavy oil according to claim 4, wherein said heating means further comprises a saucer member mounted on said heating plate to place the sample vessel thereon.

8. An apparatus for testing the stability of heavy oil according to claim 2, wherein said case body is constructed so that the height of said air bath tank from said heating means is smaller than the height of said sample heating tank from said heating means.

9. An apparatus for testing the stability of heavy oil according to claim 2, wherein said case body comprises a partition plate which separates said air bath tank from said sample heating tank so that both the tanks communicate with each other in the bottom portion.

10. An apparatus for testing the stability of heavy oil according to claim 2, wherein the bottom face of said case body is opened.

11. An apparatus for testing the stability of heavy oil according to claim 10, wherein the bottom wall of said case body is composed of a metal net.

12. An apparatus for testing the stability of heavy oil according to claim 1, wherein said temperature detecting element is a thermostat switch supported at a predetermined position above said heating means, which is turned on and off at a predetermined temperature, and said temperature control means is said thermostat switch connected in series to a circuit for supplying an electric current to said heating means.

13. An apparatus for testing the stability of heavy oil according to claim 1, wherein said temperature detecting element is a temperature switch arranged in said air bath tank, which is turned on and off at a predetermined temperature, said temperature control means is means for controlling a quantity of an electric current supplied to said heating means on receipt of a detection signal of said temperature switch, and said temperature control means is arranged within said case body outside said sample heating tank and said air bath tank.

14. An apparatus for testing the stability of heavy oil according to claim 1, wherein said filter paper is a filter paper for chromatography.

15. An apparatus for testing the stability of heavy oil according to claim 1, wherein said filter member holding means is secured and supported on said case body within said air bath tank.

16. An apparatus for testing the stability of heavy oil according to claim 1, wherein said filter paper holding means is arranged so that said filter paper holding means can be optionally put in said air bath tank and removed therefrom.

17. An apparatus for testing the stability of heavy oil according to claim 1, wherein said filter paper holding means comprises an upper plate and a lower plate, between which the filter paper is inserted and held, and openings are formed on the upper and lower plates at positions corresponding to the sample dropping portion of the filter paper.

18. An apparatus for testing the stability of heavy oil according to claim 17, wherein a part of the lower plate of said filter paper holding means is projected into the opening of the upper plate and the top face of said projection acts as an underlying cardboard for recording test data on the filter paper.

19. An apparatus for testing the stability of heavy oil according to claim 1, wherein said second cover is a lid member disposed to close said sample dropping opening, said lid member having a small hole which is formed so that the outside and inside of said air bath tank communicate with each other.

20. An apparatus for testing the stability of heavy oil according to claim 1, wherein at least one of said first and second covers is composed of a transparent material.

* * * * *